United States Patent [19]

Kurkov

[11] 4,189,608
[45] Feb. 19, 1980

[54] CARBOXYLIC ACID PREPARATION

[75] Inventor: Victor P. Kurkov, San Rafael, Calif.

[73] Assignee: Chevron Research Company, San Francisco, Calif.

[21] Appl. No.: 906,713

[22] Filed: May 17, 1978

Related U.S. Application Data

[63] Continuation-in-part of Ser. No. 659,303, Feb. 19, 1976, abandoned.

[51] Int. Cl.² ............................................. C07C 51/14
[52] U.S. Cl. ................................................... 562/519
[58] Field of Search ........................ 260/532; 562/519

[56] References Cited

U.S. PATENT DOCUMENTS

| 3,437,676 | 4/1969 | Kutepow et al. | 260/532 |
| 3,655,745 | 4/1972 | Fenton | 260/532 |
| 3,980,671 | 9/1976 | Fernholz et al. | 260/532 |

Primary Examiner—Vivian Garner
Attorney, Agent, or Firm—D. A. Newell; John Stoner, Jr.; A. T. Bertolli

[57] ABSTRACT

A process for preparing 3-butenoic acid which comprises contacting allyl alcohol with carbon monoxide and a palladium chloride catalyst at a temperature between about 50° and 300° C. and under superatmospheric pressure and wherein the reaction is carried out in a substantially anhydrous $C_2$–$C_{10}$ carboxylic acid liquid solvent. Preferably the solvent is acetic acid.

4 Claims, No Drawings

CARBOXYLIC ACID PREPARATION

CROSS-REFERENCE TO RELATED APPLICATION

This application is a continuation-in-part of U.S. application Ser. No. 659,303, filed Feb. 19, 1976, now abandoned.

BACKGROUND OF THE INVENTION

The present invention relates to the preparation of a carboxylic acid from an alcohol, particularly by a carbonylation reaction.

Carbonylation or carboxylation reactions wherein olefins are reacted with carbon monoxide and water have long been known. See, for example, U.S. Pat. No. 1,924,766 to Carpenter. U.S. Pat. No. 1,940,674, also to Carpenter, discloses reaction of an alcohol with carbon monoxide to form a carboxylic acid. U.S. Pat. No. 2,658,075 to Reppe et al refers to the carbonylation reaction with olefins as follows:

"It is well known that carboxylic acids or their functional derivatives may be obtained by treating olefins with carbon monoxide and compounds containing a replaceable hydrogen atom, such as water, alcohols, mercaptans, ammonia or primary or secondary amines or carboxylic acids. This process is generally called carbonylation."

See also U.S. Pat. No. 3,282,993, entitled "Carbonylation Process", which briefly discusses the Koch reaction wherein an olefin is reacted only with CO to form an internal anhydride which is subsequently hydrolyzed to the acid. U.S. Pat. No. 3,176,585 refers to the reaction of olefin with carbon monoxide and water as carboxylation rather than simply as carbonylation.

The present invention is particularly concerned with the carbonylation of an alcohol. Tsuji et al, "Catalytic Carbonylation of Allylic Compounds with Palladium Chloride", J. Am. Chem. Soc. 86, (1964), pp. 4350–4353 (see also Tsuji et al, U.S. Pat. No. 3,427,344) disclose the reaction of allyl alcohol with carbon monoxide in the presence of a palladium chloride catalyst. The products formed include ethyl-3-butenoate in 42% yield when the reaction is carried out in an ethanol solvent, and 3-butenoic anhydride in 19% yield when the reaction is carried out in a benzene solvent. Tsuji et al do not show formation of 3-butenoic acid.

Carbonylation of olefins in alcoholic solvent to carboxylic acid esters in the presence of palladium compounds is described by K. Bittler et al (Angew. Chem. Internat. Edit., 1(5), 329, 1968). In one example, allyl alcohol was converted to methyl 3-butenoate in 65% yield. In order to convert this product to 3-butenoic acid, which is preferred for certain applications, additional processing steps are required, i.e., hydrolysis and purification.

A laboratory synthesis of 3-butenoic acid is described in Org. Synthesis 24,29 (1944). In this synthesis, allyl chloride is converted to 3-butenenitrile with CuCN, which is then hydrolyzed by concentrated HCl to 3-butenoic acid in about 60% over-all yield.

SUMMARY OF THE INVENTION

According to the present invention, a process is provided for preparing 3-butenoic acid, which process comprises contacting allyl alcohol with carbon monoxide and a palladium chloride catalyst at a temperature between about 50° and 300° C. and under superatomspheric pressure and wherein the reaction is carried out in a substantially anhydrous $C_2$–$C_{10}$ carboxylic acid liquid solvent.

Preferred operating conditions for the method of the present invention are as follows:

|  | Preferred | More Preferred | Most Preferred |
|---|---|---|---|
| Temperature, °C. | 50–300 | 60–250 | 75–200 |
| Pressure, psig | 100–10,000 | 200–5000 | 500–2000 |
| Feed | — | — | Allyl alcohol |
| Solvent | $C_2$–$C_{10}$ carboxylic acid | — | Acetic acid |
| Catalyst | Palladium chloride | — | $PdCl_2$ |

In most general terms, the palladium catalyst can be described as: $L_nPdX_2$, where L = nitriles or phosphines or amines; n = 0 or 2; and X = Cl. $PdCl_2$ is the preferred catalyst.

As used herein, the term substantially anhydrous $C_2$–$C_{10}$ carboxylic acid means an acid relatively free of water, i.e., one having not more than 5 weight percent of water. The preferred carboxylic acids are the saturated fatty acids. Typical examples are glacial acetic acid or anhydrous propionic acid.

The 3-butenoic acid produced by the process of the present invention is advantageously used to produce gamma-butyrolactone and further to produce 2-pyrrolidone as described in my commonly assigned application entitled "Alpha-Beta-Butenolide Preparation", Ser. No. 671,881, filed on Mar. 29, 1976, now U.S. Pat. No. 4,031,114, the disclosure of which application is incorporated herein by reference.

EXAMPLES I–VII

Examples I–VII were carried out as follows. A 625-ml Hastelloy rocker bomb was charged with reactants, sealed and flushed with CO. The bomb was agitated by rocking and was rapidly heated to the reaction temperature. CO pressure was adjusted to the desired value and the reaction continued at constant pressure for the time indicated in Table I.

After the reaction was complete, the bomb was cooled down, vented, and the product analyzed by gas chromatography. The product from run II was distilled to give 62 g of 3-butenoic acid. The boiling point was 38°–43° C. at 10.6 mm Hg. Infrared and nuclear magnetic resonance spectra of this product were identical to the spectra of an authentic sample.

As can be seen from the examples, using the carboxylic acid solvent and the preferred palladium chloride catalyst results in surprisingly high yields of 3-butenoic acid, compared to, for instance, Example IV, wherein a carboxylic acid solvent was not used (acetonitrile was used).

TABLE I - EXAMPLES I-VII

| | I<br>B2163-27 | II<br>B2163-25 | III<br>B2163-30 | IV<br>B2408-29 | V<br>B2408-14 | VI<br>B2408-12 | VII<br>B2231-12 |
|---|---|---|---|---|---|---|---|
| Solvent, ml | HOAc, 200 | HOAc, 200 | HOAc, 200 | $CH_3CN$, 200 | HOAc, 100 | HOAc, 100 | HOAc, 100 |
| Allyl Alcohol, mol | .97 | .97 | .97 | .97 | .48 | .48 | .48 |
| Toluene, ml | — | — | — | — | 20 | 20 | 10 |
| Catalyst, mmol | $PdCl_2$, 10 | $CuCl_2$, 120<br>$PdCl_2$, 10<br>LiCl, 30 | $CuCl_2$, 120 | $PdCl_2$, 10 | $(\phi CN)_2PdCl_2$, 5 | $PdCl_2$, 5<br>$\phi_3P$, 25 | $PtCl_2$, 5 |
| CO pressure, psig | 1,300 | 1,300 | 1,300 | 1,300 | 1,300 | 1,300 | 1,300 |
| Temperature, °C. | 80 | 80 | 80 | 80 | 80 | 80 | 80 |
| Time, hrs. | 21 | 21 | 16 | 21 | 16 | 16 | 17 |
| Conversion % | 78 | 100 | — | 100 | 80 | 14 | 100 |
| Yield of 3-butenoic acid, mol % | 82 | 77 | 0 | 40 | 72 | 100 | 7 |

Note:
$Pd(OAc)_2$ was inactive (0% conv, 0% yield)
$\phi$ indicates phenyl

What is claimed is:

1. A process for preparing 3-butenoic acid which comprises contacting allyl alcohol with carbon monoxide and a palladium chloride catalyst at a temperature between about 50° and 300° C. and under superatmospheric pressure and wherein the reaction is carried out in a substantially anhydrous $C_2$–$C_{10}$ carboxylic acid liquid solvent.

2. A process in accordance with claim 1 wherein the solvent is acetic acid.

3. A process in accordance with claim 1 wherein the temperature is between 75° and 200° C.

4. A process in accordance with claim 1 wherein the carbon monoxide pressure is between 500 and 2000 psig.